US008202916B2

(12) United States Patent
Pawlak et al.

(10) Patent No.: US 8,202,916 B2
(45) Date of Patent: Jun. 19, 2012

(54) METHOD OF AND APPARATUS FOR PRODUCING METHANOL

(75) Inventors: Nathan A. Pawlak, Walloon Lake, MI (US); Vladimir I. Vedeneev, Moscow (RU); Alexander L. Tots, Moscow (RU)

(73) Assignee: Gas Technologies LLC, Walloon Lake, MI (US)

( * ) Notice: Subject to any disclaimer, the term of this patent is extended or adjusted under 35 U.S.C. 154(b) by 443 days.

(21) Appl. No.: 11/319,093

(22) Filed: Dec. 27, 2005

(65) Prior Publication Data

US 2006/0122283 A1    Jun. 8, 2006

(51) Int. Cl.
  *B01J 8/00*    (2006.01)
  *C07C 27/14*   (2006.01)
  *F28D 21/00*   (2006.01)
(52) U.S. Cl. ......... 518/703; 422/187; 422/207; 518/712
(58) Field of Classification Search .................. 422/187, 422/198–208; 518/702, 703, 712
  See application file for complete search history.

(56) References Cited

U.S. PATENT DOCUMENTS

| | | | |
|---|---|---|---|
| 1,038,547 A | 9/1912 | Fernekes |
| 1,500,080 A | 7/1924 | Kloppenburg |
| 1,776,771 A | 9/1930 | Boomer |
| 2,196,188 A | 9/1930 | Bone et al. |
| 2,244,241 A | 6/1941 | Bryce |
| 2,384,028 A | 9/1945 | Hall |
| 2,467,993 A | 4/1949 | Rossman |
| 2,722,553 A | 11/1955 | Mullen |
| 2,922,809 A | 1/1960 | Oberdorfer, Jr. |
| 3,027,411 A | 3/1962 | Murphy |
| 3,130,026 A | 4/1964 | Becker |
| 3,145,220 A | 8/1964 | Bartok |
| 3,232,991 A | 2/1966 | Magee |
| 3,483,229 A | 12/1969 | Bernard |
| 3,689,575 A | 9/1972 | Tarhan |
| 3,718,006 A | 2/1973 | Ranke |
| 3,920,717 A | 11/1975 | Marion |
| 3,940,428 A | 2/1976 | Connell et al. |
| 3,975,172 A | 8/1976 | Ranke |
| 3,977,203 A | 8/1976 | Hinton et al. |
| 3,993,457 A | 11/1976 | Cahn et al. |
| 4,067,972 A | 1/1978 | Oswald et al. |
| 4,144,314 A | 3/1979 | Doerges et al. |
| 4,149,940 A | 4/1979 | Pinto |
| 4,152,407 A | 5/1979 | Fuchs |
| 4,203,915 A | 5/1980 | Supp et al. |
| 4,243,457 A | 1/1981 | Mayumi et al. |
| 4,243,613 A * | 1/1981 | Brockhaus et al. ........... 568/482 |
| 4,252,548 A | 2/1981 | Markbreiter et al. |
| 4,271,086 A | 6/1981 | Supp et al. |
| 4,289,709 A | 9/1981 | Kaiser |
| 4,289,710 A | 9/1981 | Kaiser |
| 4,311,671 A | 1/1982 | Notman |
| 4,312,955 A | 1/1982 | Bartley |
| 4,324,567 A | 4/1982 | Ranke et al. |
| 4,346,179 A | 8/1982 | Sugier et al. |
| 4,353,712 A | 10/1982 | Marion et al. |
| 4,366,260 A | 12/1982 | Wainwright et al. |
| 4,374,288 A | 2/1983 | Scragg |
| 4,386,941 A | 6/1983 | Crouch et al. |
| 4,392,869 A | 7/1983 | Marion et al. |
| 4,394,137 A | 7/1983 | Marion et al. |
| 4,400,180 A | 8/1983 | Marion et al. |
| 4,430,316 A | 2/1984 | Ranke et al. |
| 4,443,560 A | 4/1984 | Le Blanc, Jr. et al. |
| 4,476,250 A | 10/1984 | Joyner et al. |
| 4,479,810 A | 10/1984 | Marion et al. |
| 4,490,156 A | 12/1984 | Marion et al. |
| 4,530,826 A | 7/1985 | Ohashi |
| 4,540,712 A | 9/1985 | Dombek |
| 4,564,643 A | 1/1986 | Shibata et al. |
| 4,575,387 A | 3/1986 | Larne et al. |
| 4,606,741 A | 8/1986 | Moreau et al. |
| 4,608,447 A | 8/1986 | Mazanec et al. |
| 4,609,388 A | 9/1986 | Adler et al. |
| 4,614,749 A | 9/1986 | Sapienza et al. |
| 4,618,732 A | 10/1986 | Gesser et al. |
| 4,619,946 A | 10/1986 | Sapienza et al. |
| 4,623,668 A | 11/1986 | Broecker et al. |
| 4,628,065 A | 12/1986 | Prouteau et al. |
| 4,628,066 A | 12/1986 | Bonnell et al. |
| 4,670,473 A | 6/1987 | Walker et al. |

(Continued)

FOREIGN PATENT DOCUMENTS

EP    0 790 226    12/1996

(Continued)

OTHER PUBLICATIONS

M. M. Karaveav, et al. "Technology of Synthetic Methanol", Moscow, Chemistry, 1984 pp. 72-125.
E.V. Sheverdenkin, et al., "Kinetics of Partial Oxidation of Alkanes at High Ptessures: Oxidation of Ethane and Methane-Ethane Mixtures", Theoretical Foundations of Chemical Engineering, vol. 38, No. 3, 2004, pp. 311-315.
Zang, et al., "Recent Progress in Direct Partial Oxidation of Methane to Methanol", Journal of Natural Gas Chemistry. vol. 12, No. 2, 2003, pp. 81-89.
Burch, et al. "Direct Conversion of Methane into Methanol", J. Chem. Soc., Faraday Trans. 1, 1989, 85(10), pp. 3561-3568.
Lodeng, et al., "Experimental and Modeling Study of the Selective Homogeneous Gas Phase Oxidation of Methane to Methanol", Industrial Engineerng Chemical Res., 1995, pp. 1044-1059.

(Continued)

*Primary Examiner* — Randy Boyer
(74) *Attorney, Agent, or Firm* — Brooks Kushman P.C.

(57) ABSTRACT

An apparatus and method of producing methanol includes reacting a heated hydrocarbon-containing gas and an oxygen-containing gas in a reactor; and adding a relatively cold hydrocarbon-containing gas, to be mixed directly with a mixture of the heated hydrocarbon-containing gas and the oxygen-containing gas, after formaldehyde is formed to inhibit decomposition of formaldehyde in the reactor, to provide a product stream comprising methanol and formaldehyde; and transferring heat from the product stream to the hydrocarbon-containing gas to heat the hydrocarbon containing gas.

29 Claims, 5 Drawing Sheets

U.S. PATENT DOCUMENTS

| | | | |
|---|---|---|---|
| 4,721,458 | A | 1/1988 | Conrad |
| 4,747,858 | A | 5/1988 | Gottier |
| 4,760,210 | A | 7/1988 | Sweeney |
| 4,782,096 | A | 11/1988 | Banquy |
| 4,816,121 | A | 3/1989 | Keefer |
| 4,822,393 | A | 4/1989 | Markbreiter et al. |
| 4,861,360 | A | 8/1989 | Apffel |
| 4,868,221 | A | 9/1989 | Sie et al. |
| 4,873,267 | A | 10/1989 | Sie et al. |
| 4,888,361 | A | 12/1989 | Sie et al. |
| 4,982,023 | A | 1/1991 | Han et al. |
| 5,012,029 | A | 4/1991 | Han et al. |
| 5,015,798 | A | 5/1991 | Han et al. |
| 5,063,250 | A | 11/1991 | Murayama et al. |
| 5,067,972 | A | 11/1991 | Hemmings et al. |
| 5,132,472 | A | 7/1992 | Durante et al. |
| 5,177,279 | A | 1/1993 | Harandi |
| 5,180,570 | A | 1/1993 | Lee et al. |
| 5,220,080 | A | 6/1993 | Lyons et al. |
| 5,384,335 | A | 1/1995 | Tierney et al. |
| 5,496,859 | A | 3/1996 | Fong et al. |
| 5,631,302 | A | 5/1997 | Konig et al. |
| 5,735,936 | A | 4/1998 | Minkkinen et al. |
| 5,770,630 | A | 6/1998 | Kowal et al. |
| 5,861,441 | A | 1/1999 | Waycuilis |
| 5,883,138 | A | 3/1999 | Hershkowitz et al. |
| 5,886,056 | A | 3/1999 | Hershkowitz et al. |
| 5,959,168 | A | 9/1999 | Aalst |
| 6,028,119 | A | 2/2000 | Kokubu et al. |
| 6,102,987 | A | 8/2000 | Gross et al. |
| 6,139,605 | A | 10/2000 | Cornell et al. |
| 6,153,149 | A | 11/2000 | Rabitz et al. |
| 6,159,432 | A | 12/2000 | Mallinson et al. |
| 6,267,912 | B1 | 7/2001 | Hershkowitz et al. |
| 6,300,380 | B1 | 10/2001 | Kobayashi et al. |
| 6,328,854 | B1 | 12/2001 | Sherman et al. |
| 6,342,091 | B1 | 1/2002 | Menzel et al. |
| 6,447,745 | B1 | 9/2002 | Feeley et al. |
| 6,595,291 | B1 | 7/2003 | Lia et al. |
| 6,625,988 | B2 | 9/2003 | Weisenstein et al. |
| 6,632,971 | B2 | 10/2003 | Brown et al. |
| 6,645,272 | B2 | 11/2003 | Lemaire et al. |
| 6,667,347 | B2 | 12/2003 | O'Rear et al. |
| 6,720,359 | B2 | 4/2004 | O'Rear et al. |
| 6,726,850 | B1 | 4/2004 | Reyes et al. |
| 6,736,955 | B2 | 5/2004 | Shaw |
| 6,881,389 | B2 | 4/2005 | Paulsen et al. |
| 6,881,758 | B2 | 4/2005 | Guillard et al. |
| 6,942,719 | B2 | 9/2005 | Stewart |
| 7,028,478 | B2 | 4/2006 | Prentice, III |
| 7,067,558 | B2 | 6/2006 | Grobys et al. |
| 7,071,238 | B2 | 7/2006 | Gamlin et al. |
| 7,083,662 | B2 | 8/2006 | Xu et al. |
| 7,108,838 | B2 | 9/2006 | McGee |
| 2001/0006615 | A1 | 7/2001 | Badano |
| 2002/0177741 | A1 | 11/2002 | Allison et al. |
| 2003/0032844 | A1 | 2/2003 | Seiki et al. |
| 2003/0065042 | A1 | 4/2003 | Shaw |
| 2004/0065199 | A1 | 4/2004 | Rojey et al. |
| 2004/0123523 | A1 | 7/2004 | Rong et al. |
| 2004/0171701 | A1 | 9/2004 | Shaw |
| 2006/0035986 | A1 | 2/2006 | Bichkov et al. |
| 2006/0235088 | A1 | 10/2006 | Olah et al. |
| 2006/0264683 | A1 | 11/2006 | Knox et al. |

FOREIGN PATENT DOCUMENTS

| | | |
|---|---|---|
| GB | 2159153 | 11/1985 |
| GB | 2196335 | 4/1988 |
| JP | 63001438 | 1/1988 |
| JP | 2004 315413 | 11/2004 |
| RU | 1336471 | 9/1996 |
| RU | 1469788 | 11/1996 |
| RU | 2162460 | 1/2001 |
| RU | 2 203 261 | 3/2002 |
| RU | 2200731 | 3/2003 |
| RU | 2203261 C1 * | 4/2003 |
| WO | WO 96/06901 | 3/1996 |
| WO | WO 03/031380 | 4/2003 |

OTHER PUBLICATIONS

Henni, et al., "Solubility of Carbon Dioxide in Methyldiethanolamine+Methanol+Water", Journal of Chemical Engineering Data, 1995, 40, pp. 493-495.

V.Y. Basevich, et al., "Cycle Regime of Gas Phase Oxidation Process of Methane to Methanol", 8 pages.

V.V. Bak, et al., "Technical and Economic Factors of Methanol Production by the Method of Direct Natural Gas Oxidation", 4 pages.

M. Kanniche, et al., "Technico-Economical Feasibility Study of $CO_2$ Capture, Transportation and Geo-Sequestration: A Case Study for France, Part 1: Comparison of the $CO_2$ Capture Options in IGCC System", 5 pages.

R. Bhatnagar, et al., "Methane Conversion in AC Electric Discharges at Ambient Conditions", Plenum Publishing, NY, 1995, pp. 249-264.

C. Liu, et al., "Oxidative Coupling of Methane with AC and DC Corona Discharges", Industrial & Engineering Chemistry Research, vol. 35, No. 10, 1996, pp. 3295-3301.

A. Marafee, et al., "An Experimental Study on the Oxidative Coupling of Methane in a Direct Current Corona Discharge Reactor over $Sr/La_2O_3$ Catalyst", Industrial & Engineering Chemistry Research, vol. 36, No. 3, 1997, pp. 632-637.

C. Liu, et al., "Methane Conversion to Higher Hydrocarbons in a Corona Discharge Over Metal Oxide Catalysts with OH Groups", 1997, Applied Catalysis A: General 164, pp. 21-33.

D.W. Larkin, et al., "Oxygen Pathways and Carbon Dioxide Utilization in Methane Partial Oxidation in Ambient Temperature Electric Discharges", Energy & Fuels 1998, 12, pp. 740-744.

C. Liu, et al., "Nonoxidative Methane Conversion to Acetylene over Zeolite in a Low Temperature Plasma", Journal of Catalysis 179, 1998, pp. 326-334.

K. Thanyachotpaiboon, et al., "Conversion of Methane to Higher Hydrocarbons in AC Nonequilibrium Plasmas", AIChE Journal, Oct. 1998, vol. 4, No. 10, pp. 2252-2257.

C. Liu, et al., "Experimental Investigations on the Interaction Between Plasmas and Catalyst for Plasma Catalytic Methane Conversion (PCMC) over Zeolites", Natural Gas Conversion V, Studies in Surface Science and Catalysis, vol. 119, 1998, pp. 361-366.

C. Liu, et al., "Comparative Investigations on Plasma Catalytic Methane Conversion to Higher Hydrocarbons over Zeolites", Applied Catalysis A: General 178, 1999, pp. 17-27.

D.W. Larkin, et al., "Carbon Pathways, $CO_2$ Utilization, and In Situ Product Removal in Low Temperature Plasma Methane Conversion to Methanol", Greenhouse Gas Control Technologies, 1999, pp. 397-402.

C. Liu, et al., "Modification of $N_aY$ Zeolite in a Corona Discharge and its Application for the Reduction of Carbon Dioxide", Greenhouse Gas Control Technologies, 1999, pp. 1103-1105.

C.L. Gordon, et al., "The Production of Hydrogen From Methane Using Tubular Plasma Reactors", Advances in Hydrogen Energy, 2000, pp. 57-67.

D.W. Larkin, et al., "Production of Organic Oxygenates in the Partial Oxidation of Methane in a Silent Electric Discharge Reactor", Ind. Eng. Chem. Res. 2001, 40, pp. 1594-1601.

D.W. Larkin, et al., "Product Selectivity Control and Organic Oxygenate Pathways From Partial Oxidation of Methane in a Silent Electric Discharge Reactor", Ind. Eng. Chem. Res. 2001, 40, pp. 5496-5506.

T.A. Caldwell, et al., "Partial Oxidation of Methane to Form Synthesis Gas in a Tubular AC Plasma Reactor", Studies in Surface Science and Catalysis, vol. 36: Natural Gas Conversion VI, 2001, pp. 265-270.

C.L. Gordon, et al., "Selective Hydrogenation of Acetylene to Ethylene During the Conversion of Methane in a Catalytic DC Plasma Reactor", Studies in Surface Science and Catalysis, vol. 36: Natural Gas Conversion VI, 2001, pp. 271-276.

K. Supat, et al., "Synthesis Gas Production From Partial Oxidation of Methane with Air in AC Electric Gas Discharge", Energy & Fuels, 2003, 17, pp. 474-481.

K. Supat, et al., "Combined Steam Reforming and Partial Oxidation of Methane to Synthesis Gas Under Electrical Discharge", Ind. Engr. Chem. Res., 2003, 42, p. Est: 7.2 (A-H).

V. Vedeneev, et al., "Obtaining Methanol at the Stepped Oxidation of Natural Gas", 2 pgs.

"ASPECT Advanced Sustainable Processes by Engaging Catalytic Technologies—Call for Pre-proposals & Program Outline", Sep. 16, 2003, pp. 1-14.

G. Foulds, et al., "Kinetics, Catalysis, and Reaction Engineering—Homogeneous Gas-Phase Oxidation of Methane Using Oxygen as Oxidant in an Annular Reactor", Ind. Eng. Chem. Res. 1993, 32, pp. 780-787.

D.N. Koert, et al., A flow reactor for the study of homogeneous gas-phase oxidation of hydrocarbons at pressure up to 20 atm (2 MPa), Mar. 1992, 7 pgs.

E. Ranzi, et al., "A New Comprehensive Reaction Mechanism for Combustion of Hydrocarbon Fuels", Prepared for the Twenty-Fifth International Symposium on Combustion Jul. 31-Aug. 5, 1994, Dec. 3, 1993, 23 pgs.

V. Arutyunov, "Recent Results on Fast Flow Gas-Phase Partial Oxidation of Lower Alkanes", Journal of Natural Gas Chemistry 13 (2004), 13 pgs.

* cited by examiner

METHOD OF AND APPARATUS FOR PRODUCING METHANOL

BACKGROUND OF THE INVENTION

The present invention relates to a method of and an apparatus for producing methanol.

Methods and apparatuses for conversion of methane into methanol are known. It is known to carry out a vapor-phase conversion of methane into a synthesis gas (mixture of CO and H2) with its subsequent catalytic conversion into methanol as disclosed, for example, in Karavaev M. M., Leonov B. E., et al "Technology of Synthetic Methanol", Moscow, "Chemistry" [1] 1984, pages 72-125. However, in order to realize this process it is necessary to provide a complicated equipment, to satisfy high requirements to purity of gas, to spend high quantities of energy for obtaining the synthesis gas and for its purification, to have a significant number of intermittent stages from the process. Also, for medium and small enterprises with the capacity less than 2000 t/day it is not efficient.

A method for, producing methanol is also known which includes a separate supply of a hydrocarbon-containing gas heated to 200-500° C. under pressure 2.15 MPa and an oxygen-containing gas in a mixing chamber, subsequent stages of incomplete oxidation of methane with a concentration of oxygen 1-4 volume percent with an additional introduction of reagents (metal oxide catalyst, higher gaseous hydrocarbons or oxygen containing compositions, a cold oxidizer) into the reaction zone of a reactor, cooling of the reaction mixture in a heat exchanger, separation of methanol from liquid reaction products in a partial condenser, supply of gaseous waste products to an input of the reactor as disclosed in the Russian patent no. 2,049,086. However, this method requires the use of a catalyst or additional reagents and an intense heating of the reacting gasses, which leads to a decrease of methanol yield and to an increased possibility of soot formation.

A further method of producing methanol is known, which includes a separate supply into a mixer of a hydrocarbon-containing gas (natural gas typically) and an oxygen-containing gas (air or oxygen). This mixture a subsequently supplied into a non-catalytic reactor for gas phase incomplete oxidation at pressures of 1-10 MPa during up to 1000 seconds at a temperature 300-500° C. without catalyst, return of waste reaction gasses which contain non-reacted methane for mixing with the initial hydrocarbon containing gas into the first reactor or into the second reactor (which is connected in series with the first reactor), as disclosed in the British patent document GB 2,196,335A. This method provides a high yield of methanol. However, due to significant time of reaction and relatively low per pass conversion (5-15% of methane can reacts during each passage through the reactor) this method has a low efficiency.

A further method of producing methanol by a separate supply and oxidation of hydrocarbon-containing gas and oxygen-containing gas at temperature 370-450° C. and pressure 5-10 MPa and time of contact in the reactor 0.2-0.22 sec is also known, and includes cooling of the heated reaction mixture to 330-340° C., introduction of methanol into the reactor, as disclosed in the patent document of the Soviet Union SU 1,469,788. Cooling of the reaction mixture without intermediate condensation and separation to 380-400° C. in multistage heat exchangers arranged in the reactor with subsequent supply of the mixture to 2-3 successive stages of oxidation is disclosed in the patent document of the Soviet Union 1,336,471. In the first case it is necessary to have an additional consumption and a secondary separation of methanol that leads to unavoidable losses, and in the second case it is necessary to provide additional cooling loops with circulation of additional cooling agent in them.

An apparatus for producing methanol is known, which includes a plurality of units arranged after one another and connected by pipes, in particular a mixing chamber connected to separate sources of hydrocarbon containing gas and air or oxygen, a reactor composed of an inert material with a heating element for incomplete oxidation of methane in a mixture supplied into the reactor under an excessive pressure, a condenser and a partial condenser for separation of methanol from the products of reaction, a vessel for re-circulated gaseous reaction products with a pipe for their supply into the initial hydrocarbon-containing gas or mixing chamber as disclosed in the British patent no. 2,1 96,335A. However, a significant time of presence of the reagents in the reactor reduces efficiency of the apparatus, and makes the process practically unacceptable in industrial conditions.

An apparatus which is close to the present invention is disclosed in Russian patent no. 2,162,460. It includes a source of hydrocarbon-containing gas, a compressor and a heater for compression and heating of gas, a source of oxygen-containing gas with a compressor. It further includes successively arranged reactors with alternating mixing and reaction zones and means to supply the hydrocarbon-containing gas into a first mixing zone of the reactor and the oxygen-containing zone into each mixing zone, a recuperative heat exchanger for cooling of the reaction, mixture through a wall by a stream of cold hydrocarbon-containing gas of the heated hydrocarbon-containing gas into a heater, a cooler-condenser, a partial condenser for separation of waste gasses and liquid products with a subsequent separation of methanol, a pipeline for supply of the waste gas into the initial hydrocarbon-containing gas, and a pipeline for supply of waste oxygen-containing products into the first mixing zone of the reactor.

In this apparatus however it is not possible to provide a fast withdrawal of heat of the highly exothermic reaction of oxidation of the hydrocarbon-containing gas, because of inherent limitations of the heat exchanger. This leads to the necessity to reduce the quantity of supplied hydrocarbon-containing gas and, further it reduces-the degree of conversion of the hydrocarbon-containing gas. Moreover, even with the use of oxygen as an oxidizer, it is not possible to provide an efficient re-circulation of the hydrocarbon-containing gas due to fast increase of concentration of carbon oxides in it. A significant part of the supplied oxygen is wasted for oxidation of CO into C02, which additionally reduces the degree of conversion of the initial hydrocarbon-containing gas and provides a further overheating of the reaction mixture. The apparatus also requires burning of an additional quantity of the initial hydrocarbon-containing gas in order to provide a stage of rectification of liquid products with vapor. Since it is necessary to cool the gas-liquid mixture after each reactor for separation of liquid products and subsequent heating before a next reactor, the apparatus is substantially complicated, the number of units is increased, and an additional energy is wasted.

A further method and apparatus for producing methanol is disclosed in the patent document RU 2,200,731, in which compressed heated hydrocarbon-containing gas and compressed oxygen-containing gas are introduced into mixing zones of successively arranged reactors, and the reaction is performed with a controlled heat pick-up by cooling of the reaction mixture with water condensate so that steam is obtained, and a degree of cooling of the reaction mixture is regulated by parameters of escaping steam, which is used in liquid product rectification stage.

Other patent documents such as U.S. Pat. Nos. 2,196,188; 2,722,553; 4,152,407; 4,243,613; 4,530,826; 5,177,279; 5.959,168 and International Publication WO 96/06901 discloses further solutions for transformation of hydrocarbons.

It is believed that the existing methods and apparatus for producing methanol can he further improved.

SUMMARY OF THE INVENTION

It is accordingly an object of the present invention to provide a method of and an apparatus for producing methanol, which is a further improvement of the existing methods and apparatuses.

It is another feature of the present invention to provide a method of and an apparatus for producing methanol which can be used directly on gas and gas-condensate deposits, and also at any gas consumer, such as power plants, gas distributing and gas reducing stations, chemical production facilities, etc.

In keeping with these objects and with others which will become apparent hereinafter, one feature of the present invention resides, briefly stated, in a method of producing methanol, which includes the steps of supplying into a reactor a hydrocarbon-containing gas, supplying into the reactor an oxygen containing gas; carrying out in the reactor an oxidation of said heated hydrocarbon-containing gas by oxygen of said oxygen-containing gas; and supplying into the reactor a cold hydrocarbon-containing gas to be mixed directly with a mixture of said heated hydrocarbon containing gas and said oxygen containing gas at a later stage of the reaction to produce methanol and also formaldehyde.

Another feature of the present invention is an apparatus for producing methanol, which has a reactor for receiving and reacting a hydrocarbon-containing gas with an oxygen-containing gas, to carry out in the reactor oxidation of said heated hydrocarbon containing gas by oxygen of said oxygen-containing gas; and means for supplying into the reactor a cold hydrocarbon-containing gas to be mixed directly with a mixture of said heated hydrocarbon containing gas and said oxygen containing gas at a later stage or the reaction to produce methanol and also formaldehyde.

As can be seen, in accordance with the present invention, heated hydrocarbon containing gas and air are supplied into a reaction zone or into a reactor, where a gas phase oxidation of the hydrocarbon containing gas is performed at elevated temperature and pressure in the reaction zone. The reaction mixture is cooled before extraction and the cooled reaction mixture is separated into waste gas and liquid product, the liquid products are rectified with separation of methanol, the waste gas is withdrawn, and a liquid is rectified with production of formaldehyde, wherein cold hydrocarbon containing gas is supplied into a regulation zone of the reactor to reduce the reaction temperature for example by 70-90° C. and thereby to provide a production and a redistribution of the ratio of products to produce corresponding quantities of methanol and formaldehyde.

The reaction is performed in a homogenous phase by a partial combustion without presence of a hydrogenous catalyst.

The regulating zone is provided with a device for introduction of unheated hydrocarbon containing gas for cooling of the reaction mixture by means of its turbulent mixing with the main stream.

The device for final cooling of the reaction mixture before separation can include a gas-liquid heat exchanger connected with the reactor, a partial condenser, and formaldehyde and methanol rectification units, and a device for cooling, located one after the other.

The inner wall of the reaction zone can be coated with a material which is inert to the reaction mixture. The reactor can be provided with thermal pockets for introducing devices for control of temperature in the reaction zone and for control and regulation in the regulating zone, such as for example thermocouples.

In accordance with a preferred embodiment of the present invention, the required temperature at the inlet of the reactor is provided by heating of the hydrocarbon containing gas to a needed temperature, for example in a tubular oven.

In accordance with a Preferred embodiment of the Present invention, the introduction of the cold hydrocarbon containing gas for reduction of temperature in the regulating zone can be performed by an introducing device and a temperature regulating valve arranged in the introduction line.

In accordance with a preferred embodiment of the present invention, during cooling of the reaction mixture in the gas-liquid heat exchanger, heat is transmitted to the raw liquid stream supplied into a formaldehyde rectification column, up to a desired temperature for performing rectification the input of the rectification coolant. The final cooling of the product gas stream is carried out in the cooling device. Then, the cooled gas is supplied into a partial condenser, in which dry gas is separated from raw liquids, including methanol, formaldehyde, ethanol, and water. The raw liquids, through the heat exchanger with temperature 100-120° C., are supplied into a rectification column. The temperature of the top of the column is 70-75° C., the pressure in the column is up to 0.2 MPa. Formaldehyde with a concentration up to 96% is supplied to storage or further processing, while the residue which contains methanol, ethanol, and water is supplied to the methanol rectification column with temperature at its top up to 80°. The final product is supplied to storage or further processing.

Alternatively, formaldehyde can be separated in the partial condenser from the liquid methanol product stream which would then comprise methanol, ethanol, and water by allowing formaldehyde to remain in the gaseous stream. In this case, the liquid stream exiting the partial condenser can bypass the formaldehyde rectification portion of the process and enter the methanol rectification column after having optionally passed through the gas liquid heat exchanger.

The time of presence of the reaction mixture in the reactor is 1.2 sec. The period of induction takes approximately 70% of this time, and thereafter a significant temperature increase of the mixture takes place. The content of methanol in the exiting gas, due to its high stability is 40%, while the content of the formaldehyde is 4%. In order to increase the portion of formaldehyde to 8-13% in the final product, the temperature of the reaction is reduced by 70-80° in the moment of jump after the period of induction at 0.7-1.4 sec of reaction due to the injection of the cold hydrocarbon-containing gas into the regulating zone.

When the temperature of reaction is changed from 370° C. to 450° C., the content of aldehydes is increased from 5% to 13% the content of organic acids is increased from 0.5% to 0.7%. The selectivity which is close to a maximum with respect to liquid organic products, including methanol and formaldehyde, is maintained at a concentration of oxygen in the initial gas mixture 2-2.8%.

In accordance with the present invention, the waste gasses are returned back into the process in the apparatus for gas preparation, with negligible distortion of its operation and quality of gas. Also, when the apparatus is arranged at gas power plants, the returned gas does not substantially change its caloric content.

The apparatus is ecologically clean and does not produce hazardous wastes. In contrast, in known apparatuses, it is necessary to burn up to 3 million tons per year of formaldehyde mixture when the capacity of the apparatus is 6 million tons per year.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings

DESCRIPTION OF THE PREFERRED EMBODIMENTS

Figure 1:
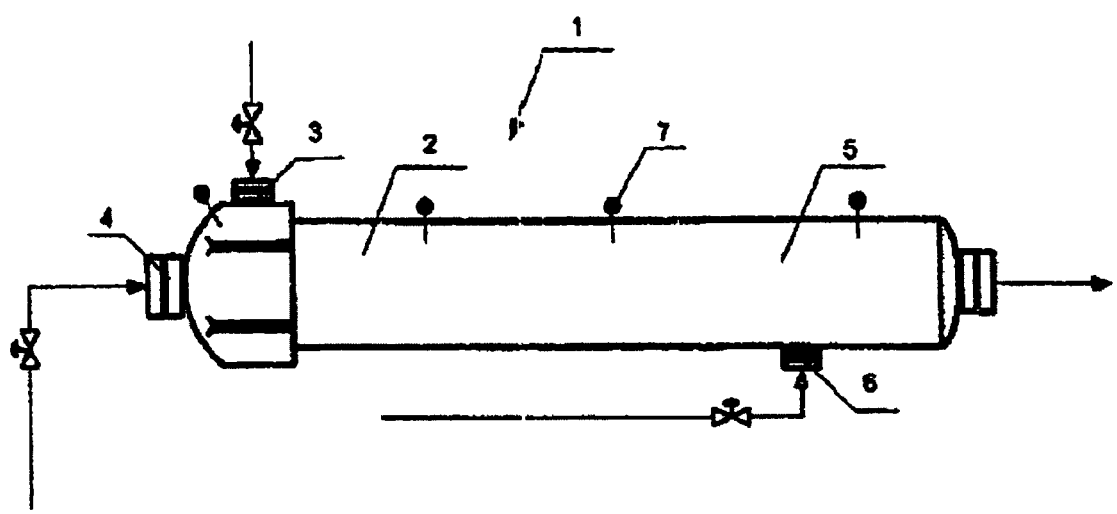
FIG. 1 is a view schematically showing a reactor of an apparatus for producing methanol in accordance with the present invention.

An apparatus for producing methanol in accordance with the present invention has a reactor which is shown in FIG. 1 and identified as a whole with reference numeral 1. In the reactor a gas phase oxidation of a hydrocarbon-containing gas is carried out. The reactor 1 has a reaction zone 2 which is provided with a device 3 for introducing a heated hydrocarbon containing gas and a device 4 for introducing an oxygen-containing gas, for example air.

The reactor further has a regulation zone 5 provided with a device 6 for introducing a cold hydrocarbon-containing gas, for reducing the temperature of reaction during operation of the apparatus. In addition, the reactor 1 is provided with thermal pockets 7 for control and regulation of temperatures in corresponding zones, provided for example with thermocouples.

Figure 2A:
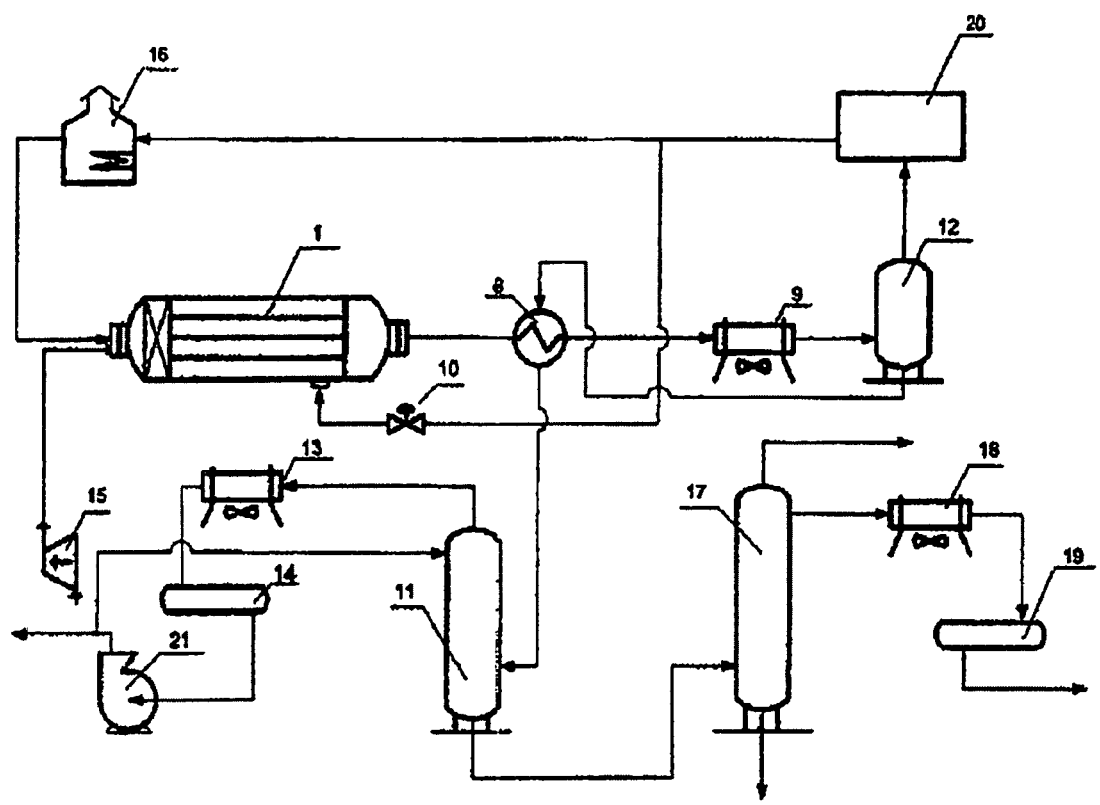
FIG. 2A is a view showing the apparatus for producing methanol, including the reactor and other devices, in accordance with the present invention.

As can be seen from FIG. 2A, the apparatus has a device for cooling the reaction mixture before separation, which includes a gas-liquid heat exchanger 8 and an cooling device 9, as well as a regulator of cold gas supply 10. The gas-liquid heat exchanger 8 is connected with a rectification unit, in particular with a rectification column 11 and a partial condenser 12. The rectification column 11 is connected with a cooling device 13, which is connected with a vessel 14. Formaldehyde is supplied from the vessel 14 by a pump 21 to storage or further processing.

The reactor 1 is connected with a compressor 15 for supply of compressed air, and with an oven 16 for heating of hydrocarbon-containing gas. The apparatus further has a unit for rectification of methanol which includes a rectification column 17, a cooling device 18 and a vessel 19, from which methanol is supplied to storage or further processing.

In operation, a hydrocarbon-containing gas with a methane content for example up to 98% is supplied from an installation for preparation of gas or any other source 20 to the oven 16, in which it is heated to temperature 430-470° C. Then the heated hydrocarbon-containing gas is supplied into the reaction zone 2 of the reactor 1. Compressed air with pressure for example 8 MPa and with a ratio 1-2.5% of oxygen is supplied by the compressor 15 also into the reaction zone 2 of the reactor 1. Oxidation reaction takes place in the reaction zone of the reactor 1. A second stream of cold or in other words not heated hydrocarbon-containing gas from the same source is supplied through the introducing device 6 into the regulation zone 5 of the reactor 1. This stream is regulated by the regulating device 10, which can be formed as a known gas supply regulating device, regulating valve or the like.

Depending on an intended mode of operation of the apparatus, in particular the intended production of methanol or formaldehyde, the reaction mixture is subjected to the reaction in the reactor without the introduction of the cold hydrocarbon-containing gas if it is desired to produce exclusively methanol, and with the introduction of the cold hydrocarbon containing gas when it is desired to produce also formaldehyde. By introduction of the cold hydrocarbon-containing gas, the temperature of the reaction is reduced for example by 70-90° so as to increase the content of formaldehyde into the separated mixture.

The reaction mixture is supplied into the heat exchanger 8 for transfer of heat to the raw liquids from the partial condenser 12, and after further cooling in the cooling device 9 is supplied with temperature 20-30° C. to the partial condenser 12. Separation of the mixture into highly volatility gases and low volatility liquids is performed in the partial condenser 12 which may condense at least some of the formaldehyde into the raw liquid stream as desired. The dry gas is returned to the gas source 20, while the raw liquids through the gas-liquid heat exchanger 8 is supplied to the rectification column 11. From the rectification column 11 vapors of formaldehyde through the cooling device 13 are supplied into the vessel 14. Formaldehyde is supplied by a pump 21 to storage or further processing. A part of formaldehyde is supplied from the vessel 14 for spraying of the rectification column 11.

Figure 2B:
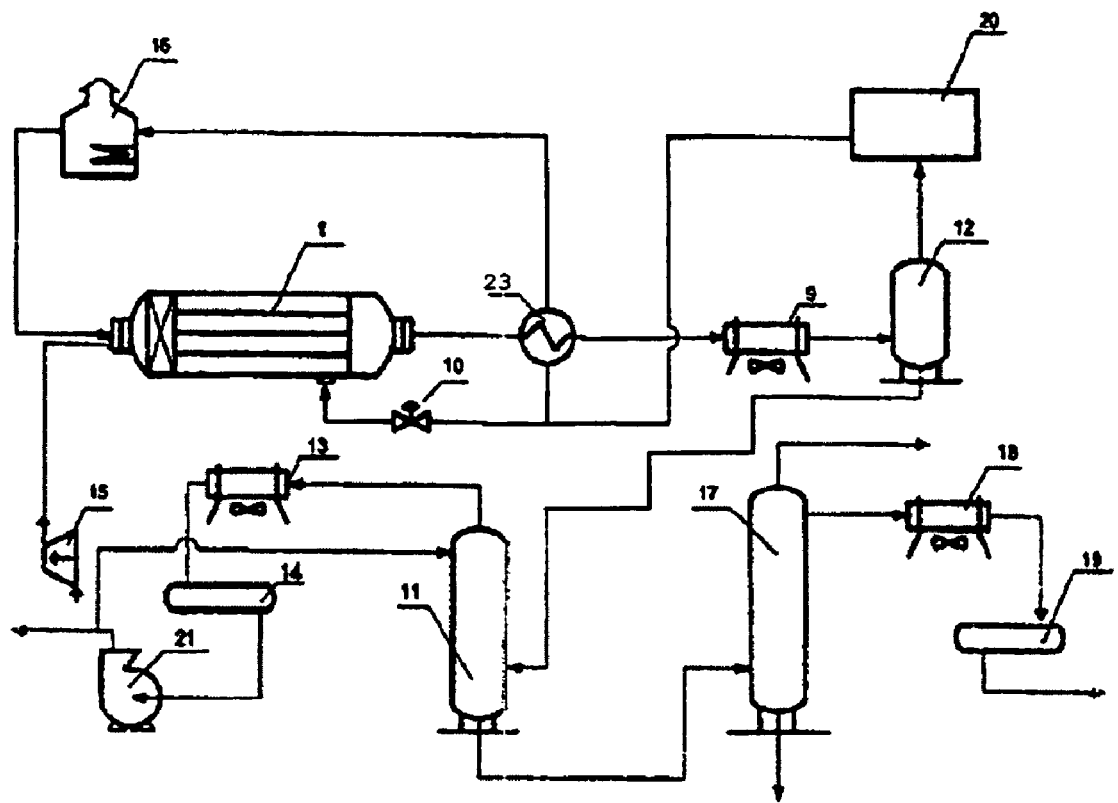
FIG. 2B is a view showing the apparatus for producing methanol, including the reactor and other devices, in accordance with an alternative embodiment of the present invention.

An alternative embodiment with the present invention would be to use the incoming hydrocarbon stream for cooling of the product gases exiting the reactor. Gas from the hydrocarbon source enters heat exchanger 23, where it cools the hot gases exiting the reactor, as seen in FIG. 2B. This process configuration lowers the duty of the cooling device 9 while simultaneously pre-heating the hydrocarbon stream before entering the furnace for heating up to the necessary temperature of the reactor. The heat exchanger may either be internal or external to the reactor.

Figure 2C:
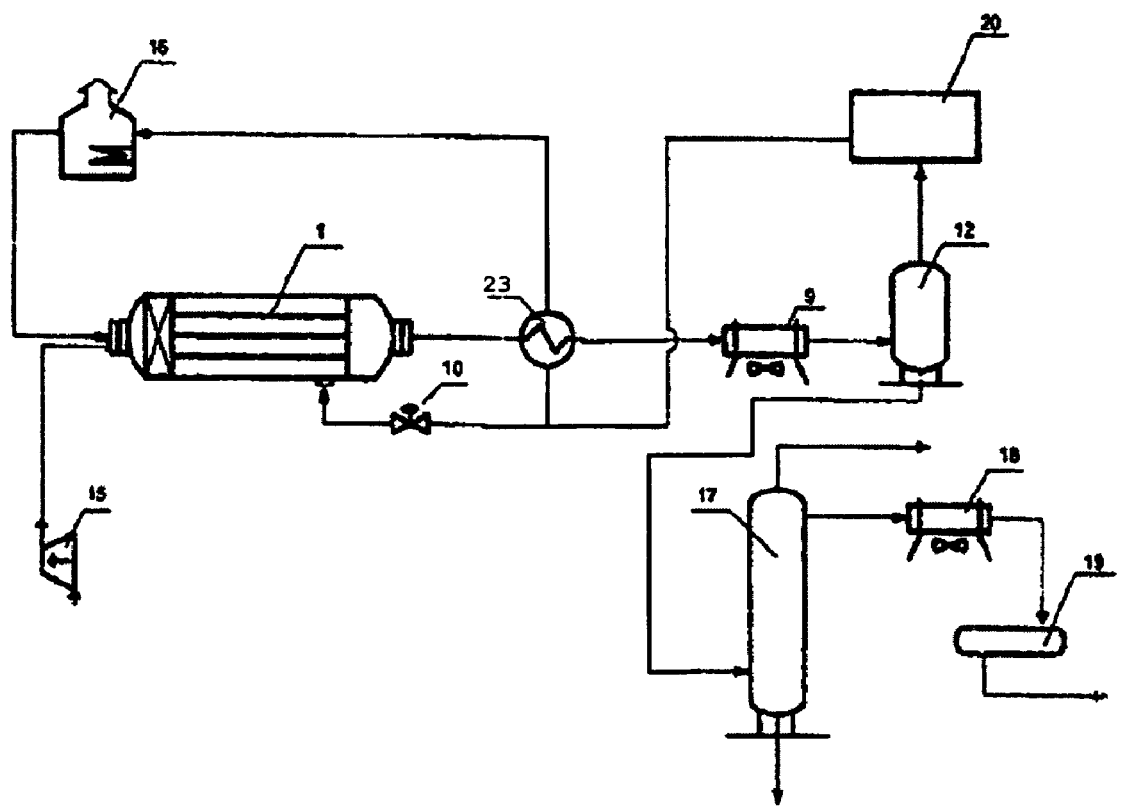
FIG. 2C is a view showing the apparatus for producing methanol, including the reactor and other devices, in accordance with a further alternative embodiment of the present invention.

Alternatively, at least some of the formaldehyde can be allowed to remain in the gas phase by operation of the partial condenser. The liquid methanol product stream which would then comprise methanol, ethanol, and water by allowing formaldehyde to remain in the gaseous stream. In this case, the liquid stream exiting the partial condenser can bypass the formaldehyde rectification portion of the process and enter the methanol rectification column after having optionally passed through the gas liquid heat exchanger as seen in FIG. 2C.

The method in accordance with the present invention and the operation of the apparatus in accordance with the present invention are illustrated by an example of operation of the apparatus with the capacity of 6,000 t/year, with cooling of the reaction mixture by 30° C.

TABLE I

| Parameters | Example 1 without cooling | Example 2 with cooling by 30° C. |
|---|---|---|
| Natural gas supply, m³/hour (kg/hour) | 56800 (40570) | 60208 (43004) |
| Gas consumption in reaction, m³/hour (kg/hour) | 1700 (1215) | 1700 (1215) |
| Conversion degree, | | |
| Oxygen concentration in reaction entry zones, | | |
| Pressure in reactor, MPa | 7 | 7 |
| Cooling in regulation zone | no cooling | direct mixing with cold gas |
| Methanol yield, kg/hour | 800 | 800 |
| Formaldehyde yield, kg/hour | 115 | 230 |
| Total organic products yield, kg/hour, | 920 | 1040 |
| Initial temperature, ° C. | | |
| Reaction temperature, ° C. | | |
| Temperature in regulation zone, ° C. | 530 | 500 |

Figure 3:
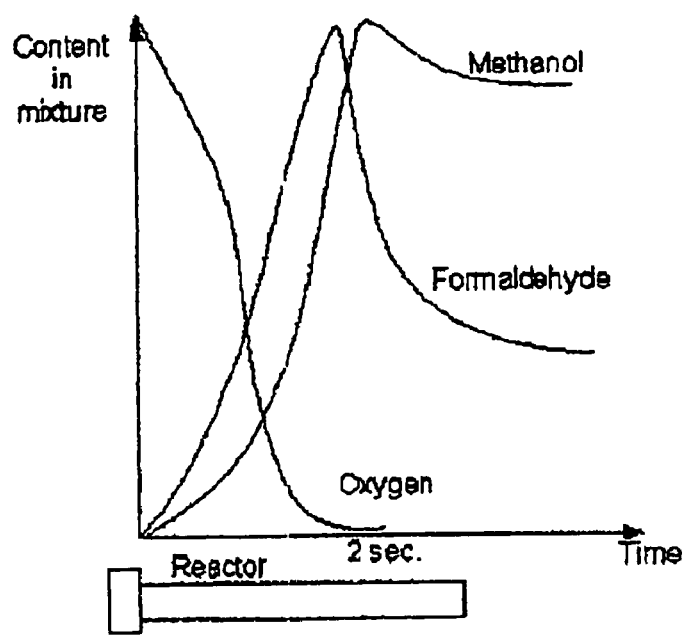
FIGS. 3 and 4 are views illustrating concentrations of oxygen, formaldehyde and methanol during reactions in accordance with the prior art and in accordance with the present invention correspondingly.
Figure 4:
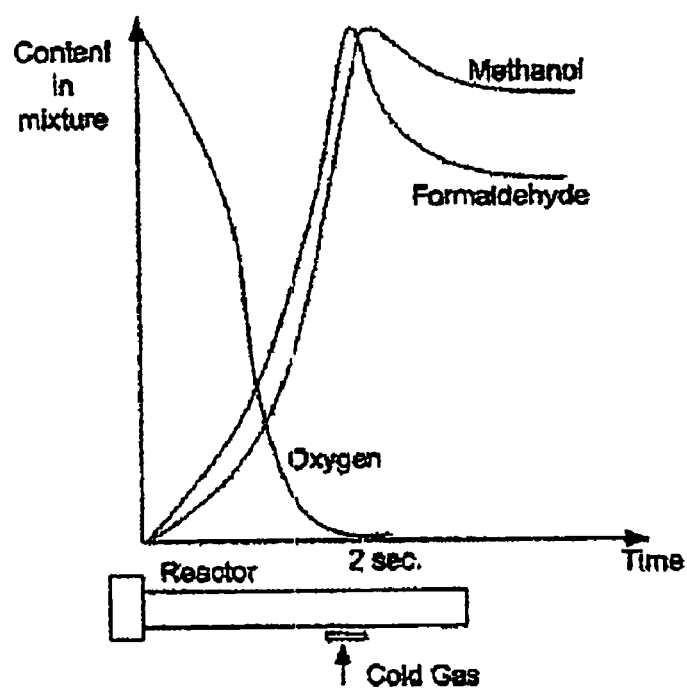

FIGS. 3 and 4 show diagrams of concentration of oxygen, formaldehyde and methanol in reactions without cooling and with cooling.

As can be seen from FIG. 3, approximately after 2 sec, oxygen is burnt completely. At this moment the reaction temperature reaches its maximum; and in the reaction mixture methanol and formaldehyde are produced with their proportions. Methanol as a more stable product at the end of the reaction reaches its maximum concentration and maintains it practically stable. Formaldehyde is less stable, and therefore with a temperature increase (the temperature increases until oxygen is burnt completely) its concentration somewhat reduces.

In the reaction with the cooling shown in FIG. 4, with introduction of the cold gas when the formation of methanol and formaldehyde is completed, the temperature of a final period of the reaction is reduced, so that formaldehyde can not decompose and reduce its concentration. Since methanol remains stable, its concentration remains constant (see Table I), while content of formaldehyde increases (on the account of other reaction products).

It will be understood that each of the elements described above, or two or more together, may also find a useful application in other types, of methods and constructions differing from the types described above.

While the invention has been illustrated and described as embodied in method of and apparatus for producing methanol, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

The invention claimed is:

1. A method comprising:
   heating a hydrocarbon-containing gas to a first temperature to form a heated hydrocarbon-containing as and supplying the heated hydrocarbon-containing gas into a reactor;
   supplying into the reactor at a first point an oxygen-containing gas to oxidize the heated hydrocarbon-containing gas to produce a reaction mixture comprising methanol and formaldehyde;
   thereafter inhibiting the decomposition of formaldehyde by supplying a hydrocarbon-containing gas at a second temperature into the reactor at a second point downstream of the first point to be mixed directly with the reaction mixture, the second temperature being less than the first temperature wherein formation of methanol and formaldehyde is substantially completed at the second point; and
   transferring heat from a resulting product stream compromising methanol and formaldehyde to the hydrocarbon-containing gas to heat the hydrocarbon-containing gas.

2. A method as defined in claim 1, wherein the oxidation is partial oxidation without a catalyst, and wherein the mixture is substantially homogeneous.

3. A method as defined in claim 1, wherein the transfer of heat from the product stream to the hydrocarbon-containing gas at least partially heats the hydrocarbon-containing gas which is thereafter further heated to provide the heated hydrocarbon-containing gas.

4. A method as defined in claim 1, wherein heat is transferred from the product stream to the hydrocarbon-containing gas in a heat exchange portion of the reactor comprises a downstream portion of the reactor.

5. A method as in claim 4, wherein the heat exchange portion of the reactor comprises a downstream portion of the reactor.

6. A method as in claim 4, wherein the heat exchange portion of the reactor comprises a heat exchanger encompassing at least a portion of the reactor.

7. A method as defined in claim 1, wherein said supplying of the cold hydrocarbon containing gas includes adjusting the quantity of the cold hydrocarbon-containing gas so to regulate the extent of the decomposition of formaldehyde in the reactor.

8. A method as defined in claim 1, wherein the product stream comprises a relatively high volatility component and a relatively low volatility component and wherein the high and low volatility components are separated from one another.

9. A method as in claim 8, wherein the relatively high volatility component comprises at least a portion of the formaldehyde of the product stream.

10. A method as in claim 9, wherein the high volatility component comprises substantially all of the formaldehyde and the low volatility component comprises methanol, ethanol, and water and subsequent processing provides a relatively purified methanol stream.

11. A method as in claim 8, wherein the relatively low volatility component comprises at least a portion of the formaldehyde of the product stream.

12. A method as in claim 11, wherein the low volatility component comprises substantially all of the formaldehyde and subsequent processing separates formaldehyde from less volatile components and provides relatively purified formaldehyde; and optionally, subsequent processing provides relatively purified methanol.

13. A method as in claim 1, wherein the relatively cold hydrocarbon containing gas is colder than the heated hydrocarbon containing gas.

14. A method as defined in claim 1, wherein the temperature of the reaction mixture is reduced by at least 30° C.

15. A method as defined in claim 1, wherein the temperature of the reaction mixture is reduced by 70° C. to 90° C.

16. An apparatus comprising:
a reactor;
a first hydrocarbon-containing gas supply means for supplying into the reactor a hydrocarbon containing gas at a first point;
means for supplying into the reactor an oxygen containing gas at a second point, so that in said reactor a heated hydrocarbon containing gas is oxidized to produce a reaction mixture comprising methanol and formaldehyde;
a second hydrocarbon-containing gas supply means, at a third point downstream of the first point and the second point, wherein at the third point the formation of methanol and formaldehyde is substantially completed, for supplying into the reactor a relatively cold hydrocarbon containing gas to the directly mixed with the reaction mixture to inhibit the decomposition of formaldehyde and to produce a product stream comprising formaldehyde and methanol; and
heat exchange means for transferring heat from the product stream to the hydrocarbon-containing gas supplied by the first supply means at the first point.

17. An apparatus as defined in claim 16 and further comprising a heater disposed between the heat exchange means and the reactor for further preheating the hydrocarbon containing gas prior to its supplying into the reactor.

18. An apparatus as defined in claim 16, wherein said heat exchange means comprises a heat exchange portion of the reactor, an external heat exchanger or both.

19. The apparatus of claim 18, wherein the heat exchange means comprises an external heat exchanger downstream of the reactor.

20. The apparatus of claim 18, wherein the heat exchange portion of the reactor comprises a downstream portion of the reactor.

21. The apparatus of claim 18, wherein the heat exchange portion of the reactor comprises a heat exchanger encompassing at least a portion of the reactor.

22. An apparatus as in claim 16, wherein control means adjusts the second supply means based on one or more operating parameters.

23. An apparatus as in claim 22, wherein the one or more parameters comprises temperature.

24. An apparatus as in claim 16 further comprising a condenser that condenses a relatively low volatility component of the product stream for separation from a relatively high volatility component of the product stream.

25. An apparatus as in claim 24 further comprising a formaldehyde rectifier downstream of the condenser.

26. An apparatus as in claim 24 further compromising a methanol rectifier downstream of the condenser.

27. A method comprising:
heating a hydrocarbon-containing gas;
injecting the heated hydrocarbon-containing gas and an oxygen-containing gas into a reaction zone of a reactor, wherein the reaction zone is upstream of a regulation zone of the reactor, to produce a reaction mixture comprising methanol and formaldehyde;
injecting a relatively cold hydrocarbon-containing gas into the regulation zone to directly mix with the reaction mixture and inhibit the decomposition of formaldehyde by reducing the reaction temperature, and to produce a product stream comprising methanol and formaldehyde; and
transferring heat from the product stream to the hydrocarbon-containing gas.

28. A method as defined in claim 27, wherein the temperature of the reaction mixture is reduced by at least 30° C.

29. A method as defined in claim 27, wherein the temperature of the reaction mixture is reduced by 70° C. to 90° C.

* * * * *

UNITED STATES PATENT AND TRADEMARK OFFICE
CERTIFICATE OF CORRECTION

| | | |
|---|---|---|
| PATENT NO. | : 8,202,916 B2 | Page 1 of 1 |
| APPLICATION NO. | : 11/319093 | |
| DATED | : June 19, 2012 | |
| INVENTOR(S) | : Nathan A. Pawlak et al. | |

It is certified that error appears in the above-identified patent and that said Letters Patent is hereby corrected as shown below:

Column 8, Line 4, Claim 1:

After "hydrocarbon-containing" delete "as" and insert -- gas --.

Column 8, Line 20-21, Claim 1:

After "product stream" delete "compromising" and insert -- comprising --.

Column 8, Line 33-34, Claim 4:

After "portion of the" delete "reactor comprises a downstream portion of the reactor"

and insert

-- reactor, in an external heat exchanger downstream of the reactor, or both --.

Column 9, Line 23, Claim 16:

After "hydrocarbon containing gas" delete "to the directly mixed"

and insert -- to be directly mixed --.

Signed and Sealed this
Eighteenth Day of September, 2012

David J. Kappos
*Director of the United States Patent and Trademark Office*